United States Patent
Schon et al.

(10) Patent No.: US 9,775,717 B2
(45) Date of Patent: Oct. 3, 2017

(54) SUBTALAR JOINT PROSTHESEIS AND ITS METHOD OF IMPLANTATION

(76) Inventors: Lew C. Schon, Baltimore, MD (US); Christopher Chiodo, Walpole, MA (US); Brent G. Parks, West Friendship, MD (US); David Aaron, Reistertown, MD (US); Zeynep B. Dine, Baltimore, MD (US)

(*) Notice: Subject to any disclaimer, the term of this patent is extended or adjusted under 35 U.S.C. 154(b) by 0 days.

(21) Appl. No.: 14/239,195

(22) PCT Filed: Aug. 15, 2011

(86) PCT No.: PCT/US2011/047716
§ 371 (c)(1),
(2), (4) Date: Apr. 29, 2014

(87) PCT Pub. No.: WO2013/025194
PCT Pub. Date: Feb. 21, 2013

(65) Prior Publication Data
US 2015/0051706 A1    Feb. 19, 2015

(51) Int. Cl.
*A61F 2/42*      (2006.01)
*A61F 2/30*      (2006.01)

(52) U.S. Cl.
CPC .......... *A61F 2/4225* (2013.01); *A61F 2/4202* (2013.01); *A61F 2002/30879* (2013.01); *A61F 2002/4207* (2013.01); *A61F 2002/4217* (2013.01); *A61F 2002/4223* (2013.01)

(58) Field of Classification Search
CPC ............................................. A61F 2002/4207
See application file for complete search history.

(56) References Cited

U.S. PATENT DOCUMENTS

| | | | |
|---|---|---|---|
| 7,025,790 B2 | 4/2006 | Parks et al. | |
| 2004/0133276 A1 | 7/2004 | Lang et al. | |
| 2005/0049711 A1* | 3/2005 | Ball | A61F 2/4202 623/21.18 |
| 2006/0142870 A1 | 6/2006 | Robinson et al. | |
| 2010/0057216 A1 | 3/2010 | Gannoe et al. | |
| 2010/0280625 A1 | 11/2010 | Sanders et al. | |
| 2012/0271430 A1* | 10/2012 | Arnett | A61F 2/4202 623/21.18 |

* cited by examiner

*Primary Examiner* — Thomas J Sweet
*Assistant Examiner* — Wade P Schutte
(74) *Attorney, Agent, or Firm* — Larry J. Guffey

(57) ABSTRACT

A subtalar joint prosthesis that is adapted to replace the natural subtalar joint that exists between a patient's talus and calcaneus bones includes talar and calcaneal components. Each of these is configured to have a shape that is herein defined as being a portion of the boundary surface of a frustum. Meanwhile, these components' inner surfaces are configured to: (a) generally follow the anatomic contour of the original joint surface to which each component is to be attached, and (b) minimize each components's average thickness, consistent with providing sufficient strength and rigidity for the components, so as to require minimum bone resection for the implantation of these components.

17 Claims, 4 Drawing Sheets

SUBTALAR JOINT PROSTHESEIS AND ITS METHOD OF IMPLANTATION

CROSS-REFERENCE TO RELATED APPLICATION

This application claims the benefit of PCT Patent Application No. PCT/US2011/047716, filed Aug. 15, 2011 by the present inventors. The teachings of this earlier application are incorporated herein by reference to the extent that they do not conflict with the teaching herein.

BACKGROUND OF THE INVENTION

1. Field of the Invention

This invention relates to surgery and orthopedic instrumentation. More particularly, this invention relates to a subtalar joint prosthesis and the surgical procedure and apparatus for its implantation.

2. Description of Prior Art

For many years there has been considerable interest and activity with respect to joint replacement in the foot and ankle, in which the degenerative articular surfaces of a joint are removed and replaced with an artificial joint, called a prosthesis, as a viable approach for the treatment of diseased or injured joints. Among the joints that can be considered for treatment in this manner is the subtalar joint, otherwise known as the talocalcaneal joint, which is comprised of the articulation between the talus and calcaneus bones. It is an essential joint of the foot, since it contributes to ankle stability, and the stress distribution and collaborative function of the hindfoot complex. Severe pain in this joint can also cause instability, limping and wear on other joints.

Fusion has long been a treatment for subtalar joint arthritis and disease. This approach has its drawbacks. It is known that limiting the motion in one joint will result in greater load distribution in adjacent joints, which can further degenerative disease. Other treatments include orthotics, braces, physical therapy and cortisone shots.

Many types of ankle joint prostheses have been developed over the past thirty years. Their use usually requires a surgeon to create, at the joint which is to be treated, a space which can accommodate the prosthesis. The size of the prosthesis will typically result in the resection of a significant amount of bone and the compromising of adjoining critical bony and soft tissue structures. This situation can lead to the diminishment over time of the stability of the orientation of such prosthesis and their ultimate failure.

Despite the development of many types of ankle joint prostheses, none has ever been developed for the subtalar joint. Thus, there is a need for the development of a subtalar joint prosthesis. There is also a need for the development of a surgical method to install such a prosthesis that will minimize the amount of bone loss associated with its implantation and therefore allowance for the preservation of the strongest portions of the distal talus and proximal calcaneus.

SUMMARY OF THE INVENTION

Recognizing the need for the development of a subtalar joint prosthesis and the surgical methods necessary for its implantation, the present invention is generally directed to satisfying the needs set forth above.

In accordance with the present invention, a subtalar joint prosthesis for replacing, after the necessary surgical preparation of the appropriate joint-related portions of the patient's talus and calcaneus bones, a patient's natural subtalar joint includes talar and calcaneal components. Both of these components have inner and outer surfaces and medial and lateral sides. Their inner surfaces are configured to generally follow the anatomic contour of the original adjoining bone joint surface to which these components' inner surfaces are to be attached.

The thickness of each of these components is minimized, consistent with providing sufficient strength and rigidity for the components, so as to require minimum bone resection for their implantation.

Meanwhile, their outer surfaces have complimentary geometries so as to allow them to move with respect to one another in such a manner as to functionally produce (duplicate or closely duplicate) the approximate motion found in a patient's natural subtalar joint.

In general, these components are further configured so that each has a shape that is herein defined as being a portion-of-the-boundary-surface-of-a-frustum.

Alternatively, the present invention may be described as a method of replacing a natural subtalar joint that exists between a patient's talus and calcaneus bones after surgical preparation of the appropriate joint-related portions of these bones so as to accommodate a subtalar joint prosthesis, and wherein this method includes the steps of: (a) utilizing a means both for measuring the geometric contours of a patient's natural subtalar joint to determine the shape which the subtalar joint prosthesis must take in order to allow for minimal bone resection during the surgical preparation of the appropriate joint-related portions of the bones and for surgically reproducing this determined shape of the necessary subtalar joint prosthesis in the appropriate joint-related portions of these bones during this resection, (b) fabricating a subtalar joint prosthesis having this measured and determined shape, and (c) inserting such a subtalar joint prosthesis in the surgically prepared portions of these bones. In a preferred embodiment, this means both for measuring the patient's natural subtalar joint and for surgically reproducing this determined shape of the required subtalar joint prosthesis in the joint-related portions of these bones includes the combination of an elongated shaft, an alignment base with a guide therein and a ball and socket member, and wherein the elongated shaft's central point passes through the ball and socket member and its distal end passes through the guide and wherein this combination has a configuration that allows the shaft's proximate end to be placed in the patient's natural subtalar joint for performing these tasks of measuring and surgically preparing the joint-related portions of these bones.

Thus, there has been summarized above, rather broadly and understanding that there are other preferred embodiments which have not been summarized above, the present invention in order that the detailed description that follows may be better understood and appreciated. There are, of course, additional features of the invention that will be described hereinafter and which will form the subject matter of the later presented claims to this invention.

DETAILED DESCRIPTION OF THE PREFERRED EMBODIMENT

Figure 1A:
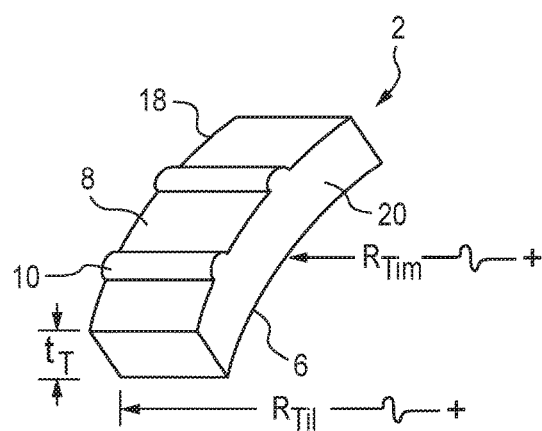
FIGS. 1A and 1B show, respectively, perspective views of the inner and outer surfaces of a preferred embodiment of the talar component of the present invention.
Figure 1B:
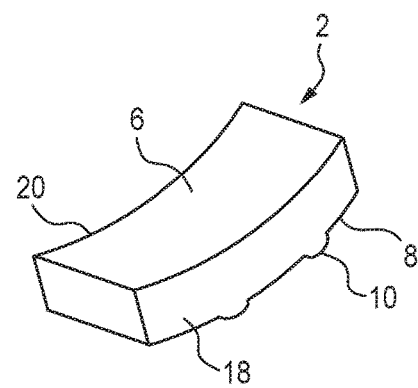
Figure 2A:
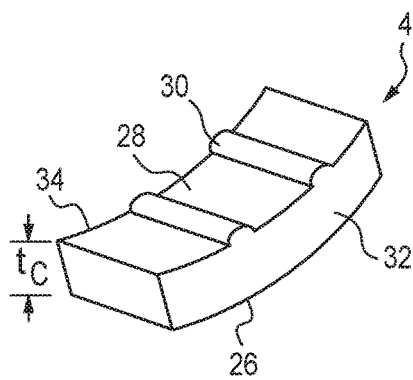
FIGS. 2A and 2B show, respectively, perspective views of the inner and outer surfaces of a preferred embodiment of the calcaneal component of the present invention.
Figure 2B:
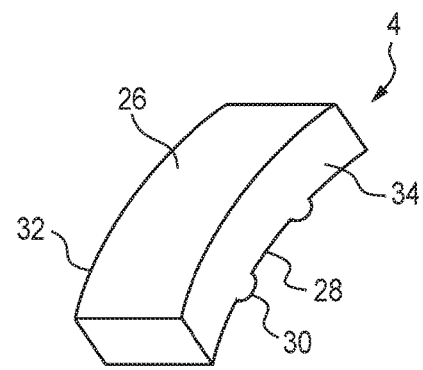

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

In a preferred embodiment, the subtalar joint prosthesis 1 of the present invention includes talar 2 and calcaneal 4 components. See FIGS. 1A-1B and 2A-2B. These components are designed so as to allow the subtalar joint prosthesis of the present invention to reproduce natural subtalar joint motion.

Figure 3:
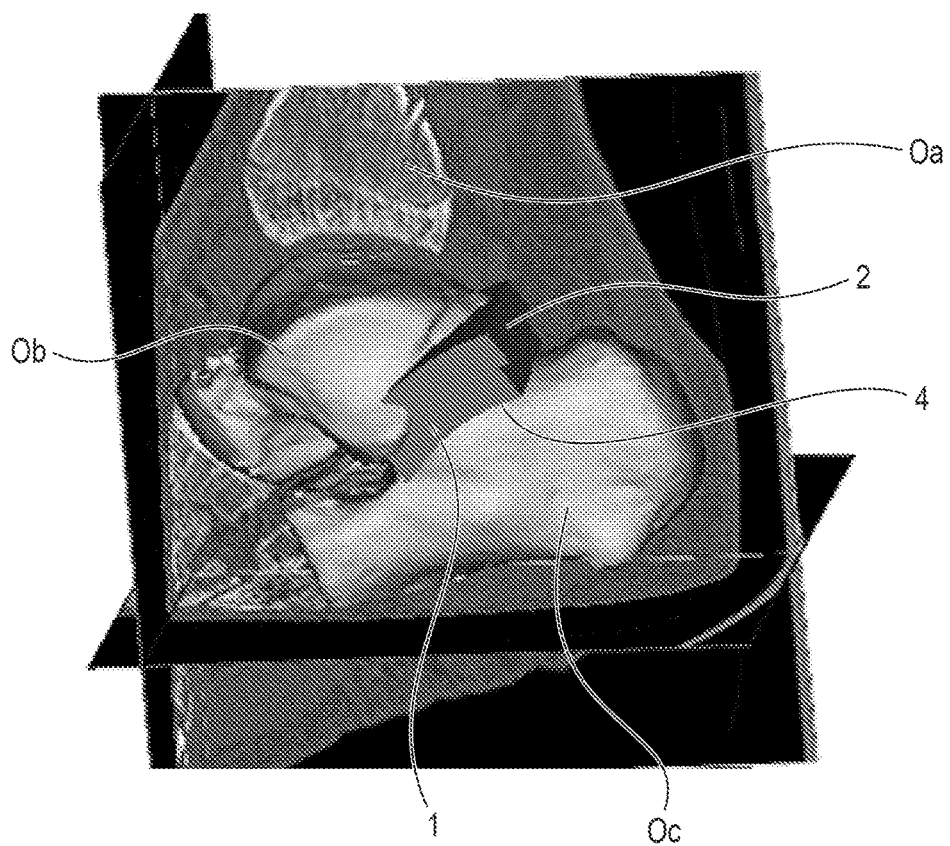
FIG. 3 shows a perspective view of these components implanted in a subtalar joint.

FIG. 3 shows these components after they have been implanted in the subtalar joint. Shown is a generally medially to lateral looking view of a patient's right foot where the tibia 0a, talus 0b, and calcaneus 0c bones can be seen.

To allow for this implantation, the surgeon has to precisely create at the subtalar joint the spaces necessary to accommodate these components. This requires the precise resection of a minimal amount of bone from the affected portions of the talus and calcaneus that comprise the joint.

Figure 4:
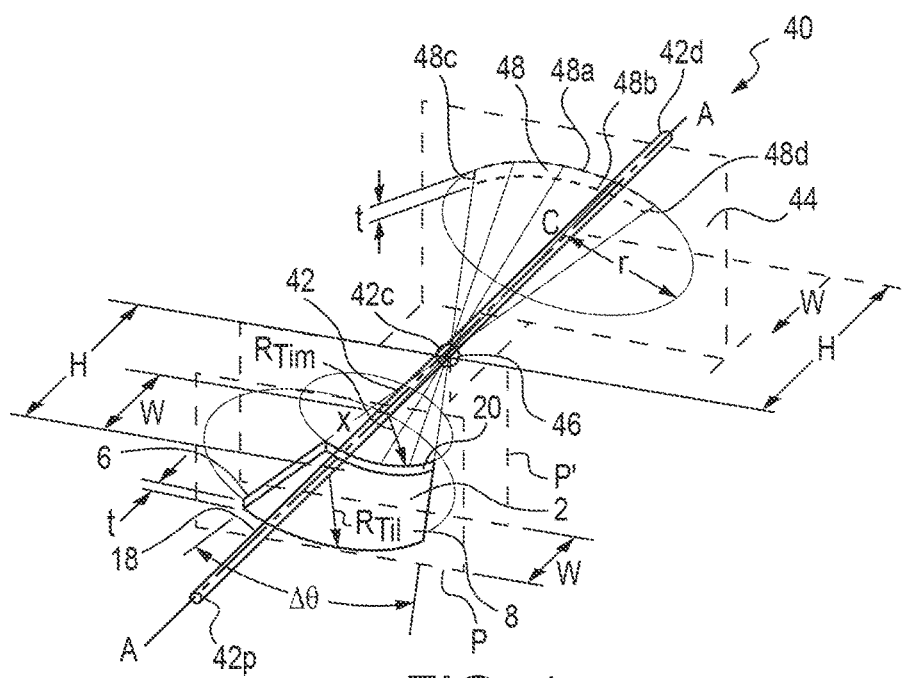
FIG. 4 illustrates how a surgery aiding device can be used to measure and create the precise subtalar joint spaces needed to accommodate the prosthesis' components.

FIG. 4 gives some idea of how such precise resections can be made such that they precisely correspond to the desired resulting shapes of the talar 2 and calcaneal 4 components. A surgery aiding device 40 is assumed, for the purpose of this discussion, to be affixed to the medial side of a patent's subtalar joint.

This device consists of a shaft 42, a mounting base and alignment base 44, a ball & socket joint or member 46 and a guide 48. When this device's base is securely locked to a patient's leg, it provides a platform on which measurement instruments can be mounted for precisely measuring the geometric contours of a patient's original subtalar joint and for mounting the cutting tools that will be used to resect the bone necessary to create the spaces for the prosthesis' components. For example, using a cutting tool that has a shaft 42 consisting of an elongated rod or member whose distal end 42d is passed through the void in the alignment base 44 that is created by the guide 48 and whose mid-point or central point 42c is passed through a hole in the ball & socket member 46, one is able to locate the cutting tool's proximal end 42p or tip in a patient's subtalar joint.

In FIG. 4, assume that the device's ball & socket joint 46 is located, for example, at the apex of a right, circular cone that extends to the right of its apex and has an axis A-A that is perpendicular to the circle that defines the cone's base and with this circle having a center point located at C and a radius, r, and with this cone's apex being at a height, H, above the cone's base. Assume also that this cone's base lies in the plane of the alignment base. Furthermore, initially assume that this guide 48 is two-dimensional and configured such that it has an outer boundary 48a which lies on the perimeter of the cone's base and a concentric inner boundary 48b which lies a specified distance, t, inside of this outer boundary and straight, parallel ends 48c, 48d whose distance apart can be defined by a specified arc segment, $\Delta\theta$, about the center of this cone's base.

Then, with these assumptions, it can be seen how this guide's geometry and various scales that are attached to the guide can be used with the mirror image of this cone that appears to the left of the apex, and where the base of the mirror image cone is assumed to be located at the site of the subtalar joint that is to be replaced, can serve to provide a means for measuring the geometric contours of a patient's natural subtalar joint to determine the shape which the subtalar joint prosthesis must take in order to allow for minimal bone resection during the surgical preparation of the appropriate joint-related portions of the bones. This is especially true if the alignment guide is allowed to move forward towards the ball & socket member a specified distance, w, so as to set the medial-lateral length or width of this prosthesis component (note: with this medial-lateral movement, it becomes a three-dimensional guide).

The geometry of this guide, which can be quite varied and complex, is clearly seen to determine the shape of any prosthesis component which is created using such a guide. The benefit of this surgery aiding device 40 and its guide 48 is that it not only can be used to precisely locate and measure the geometric contours of a patient's original subtalar joint and therefore to determine the shape which the prosthesis components should take in order to allow for minimal bone resection, but it also provides a means that allows the surgeon to reproduce these component shapes while precisely resecting this minimal amount of bone from the affected portions of the talus and calcaneus that comprise the joint which is to be replaced by the prosthesis. Thus, this device 40 is a means for both measuring the geometric contours of a patient's original subtalar joint and therefore determining the shape which the prosthesis components must take in order to allow for minimal bone resection and for allowing the surgeon to reproduce these component shapes while resecting the minimal amount of bone from the affected portions of the talus and calcaneus.

The shape of a prosthesis component formed in this manner can be described as part of the conical boundary surface of the frustum formed from the right, circular cone having its circular base of radius r in the plane P and its apex at a height H above this base (note: the base of this cone can be shaped other than just circular). The top surface of this frustum is formed by the parallel plane P' intersecting the cone's axis at a height w above its base. We hereinafter refer to such a shape as being a "portion-of-the-boundary-surface-of-a-frustum" or to such a component as being "portion-of-the-boundary-surface-of-a-frustum" shaped.

A preferred embodiment of this portion-of-the-boundary-surface-of-a-frustum shaped talar component 2 seen in FIG. 1A has a convex inner (i.e., inner with respect to the talus to which the component is attached) surface 8. This component's inner surface 8 is configured to generally follow the anatomic contour of the original talus joint surface to which this talar component is to be attached (i.e., the patient's natural talus joint surface in this instance has concave curvature to which the convex curvature of the talar component's inner surface is complimentary).

The curvature of this component's inner surface 8 can, in this instance, be defined by the two radii of curvature, the one on its lateral side, $R_{Til}$, and the one on its medial side, $R_{Tim}$, and where $R_{Til} > R_{Tim}$ since the apex of the cone from which this component can be formed lies on the medial side of the component. Alternatively, we can quantify the curvature of this surface by its average radius, $R_{Ti}$ which occurs at the midpoint between the component's lateral and medial sides. In some other instances, this radial distance can vary in other than a linear manner as a function of the distance between the component's lateral to medial sides, i.e., $R_{Ti}(x)$, where x is a coordinate that measure distance between the two sides.

In terms of our prior discussion of a frustum, this component's inner surface is seen to be formed by what we'll call the superior side of the cone whose base is partially comprised of this component's lateral side 18, with its opposite side (i.e., that closest to its apex, being what we'll define as its medial side 20.

This component's outer surface 6 can have any number of shapes, but is often shaped so that it is parallel and concentric to the shape of this component's inner surface so that the thickness, $t_T$, between these outer and inner surfaces is approximately uniform. As seen in FIG. 1A, this component's outer surface 6 has concave curvature as defined by a plane passing through this surface in an anterior to posterior direction.

Since this distance between these outer 6 and inner 8 surfaces is ultimately seen to be an important factor in the design of this prosthesis, we quantify it by taking its value at each of the various points or locations on the faces of these surfaces, and then averaging these values to define the average thickness, $t_T$, of this talar component.

An advantage of this parallel-concentric, inner and outer surfaces design is that it will ultimately lead to a prosthesis that can have a minimum thickness while also ensuring that the talar component has sufficient strength and rigidity to withstand the stresses that will be placed on this component as it is used in the prosthesis.

Achieving such a minimum thickness is important because a significant amount of bone will have to be surgically removed from that portion of the talus to which this talar component is to be attached (i.e., the joint-related portion of the talus) so as to provide room in the patient's foot for the prosthesis. Furthermore, it is known that the less bone that has to be removed (i.e., minimal bone resection), the better the chances will be for the eventual success of the prosthesis—both in terms of the health of the patient's foot (e.g., reduced bone resorption and inflammation) and lengthening the duration of the prosthesis' effectiveness. Another advantage in achieving minimum prosthesis thickness is that if the prosthesis ultimately fails or is rejected, another prosthesis may be surgically installed or if required a fusion can still be an option since minimal bone was originally removed.

While the implants above have been discussed as being formed from frustums whose bases are circular in shape, this need not be the case. For example, to form a frustum-shaped implant, one can start with a cone whose base has a uniquely shaped base perimeter or directrix that includes a combination of segments of curves, e.g., protrusion on an otherwise smooth curve of constant radius.

To facilitate fixation of this component to the talus, one or more protrusions/rails/bars 10 extend from its inner surface 8. Depending on the direction of this component's insertion into the talus, these protrusions can either be aligned along that direction of insertion or may be aligned slightly obliquely to that direction (i.e., starting more anteriorly on the lateral aspect and ending more posteriorly on the medial aspect). To accommodate these protrusions, similarly shaped recesses are made in the talus surface to which this component is to be attached.

These protrusions may take many forms; they will generally protrude perpendicular to the implants' surfaces, spanning the length of the joint space, from medial to lateral or anterior to posterior. The cross section of these protrusions may be any number of geometric shapes, including circles, half-circles, triangles, rectangles, rails, pegs (which have smaller length to width ratios), etc. In other instances the protrusions may be present more centrally on the implant surface and may take any shape, such as cylinders, convexities, cones, hemispheres, etc. In all possible instances of implant attachment, a fibular osteotomy may be performed if necessary.

In other instances, either of this prosthesis' components may be attached with a combination of screws that lock onto especially designed screw receptacles or anchor that are first implanted into the patient's talus and/or calcaneus bones. These anchors generally have an interlocking surface that is configured to mate with the screws. Additionally FDA approved products, such as bone cement, may also be used to fix implants in place. Bone void filler products and the patient's stem cells may be incorporated to avoid undesired voids arising in the joint space and to improve healing.

The calcaneal component 4 of the present invention has a concave inner (i.e., inner with respect to the calcaneus bone to which the component is attached) surface 28 that generally follows the anatomic contour of the natural, convex-curved calaneus joint surface to which the calcaneal component is to be attached. This component's shape is also describable as being a "portion-of-the-boundary-surface-of-a-frustum."

Figures 5A, 5B:
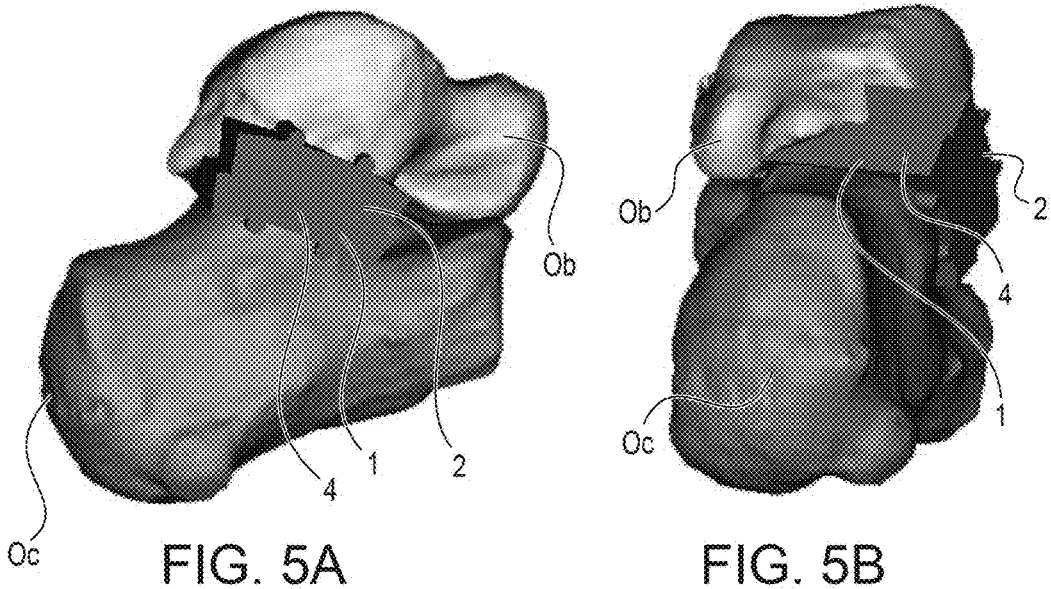
FIGS. 5A-5B show perspective views of the nesting of the present invention's talar and calcaneal components so as to create a new effective joint surface about which the adjoining talus and calcaneus bones may move.

In this embodiment, the calcaneal component's outer surface 26 has generally convex curvature that is quantified by this surface's average radius, $R_{Co}$, and is approximately equivalent to or slightly larger than the average radius, $R_{To}$, of the talar component's outer surface (note: the inferior radius of the calcaneal component would generally be the smallest, and smaller than its superior radius by amount of the calcaneal implant's thickness; the superior radius of the calcaneal component may be equal to or slightly smaller than the radius of the inferior surface of the talar component, which will also be smaller than the radius of its superior surface by the amount of the talar component's thickness). This situation allows the talar component's concave outer surface 6 to be adjoined to or nested into the calcaneal component's convex outer surface 26 so as to create a new effective joint surface about which the adjoining talus and calcaneal bones will be allowed to move. See FIGS. 5A-5B.

In general, the talar and calcaneal outer surfaces having complimentary geometry or curvature so as to allow them to move with respect to one another in such a manner as to simulate the motion in a patient's normal subtalar joint. Either of these components' outer surfaces can also be configured with one of a variety of forms of curvature or protrusions that are designed to yield various degrees or defined levels of constraint of movement with the outer surface of the adjoining component. These components would therefore be partially locked together. For example, the calcaneal component can have on its outer surface a dome that partially locks this component into the matching concavity or recess that is created in the talar component's outer surface. Similarly, the talar component's outer surface could have a dome or other protruding surface that would lock into a similarly shaped recess created in the calcaneal component's outer surface.

In terms of our prior discussion of the formation of such components with a surgery aiding device that is placed on the medial side of a patient's foot, this calcaneal component is said to have lateral 32 and medial 34 sides.

The calcaneal component has a thickness, $t_C$, between its outer and inner surfaces is often approximately uniform. Meanwhile, its average thickness, $t_C$, is usually set at a minimum value so to yield a minimal amount of bone resection from said joint-related portion of the calcaneus while providing sufficient strength and rigidity in the component.

Figures 6A, 6B:
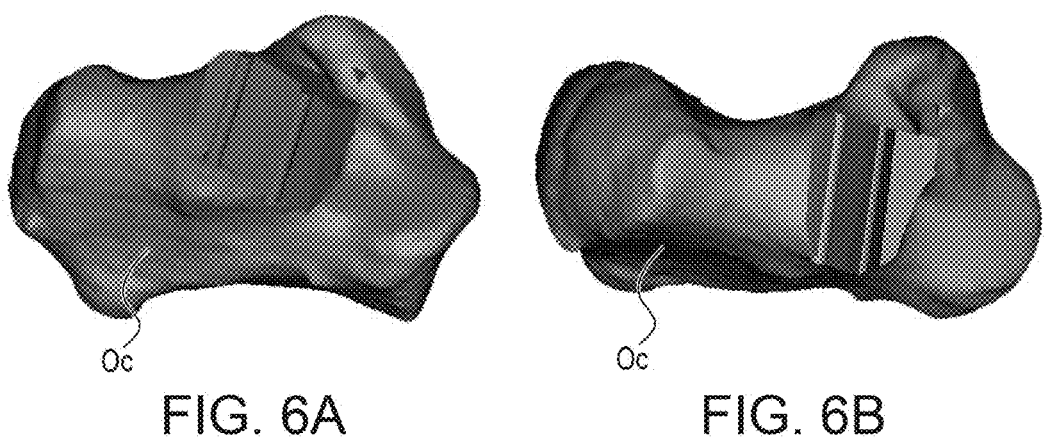
FIGS. 6A-6B show examples of the locations and orientations on the superior, medial, anterior portions of the calcaneus bone on which its calcaneal component can be affixed.
Figure 7A:
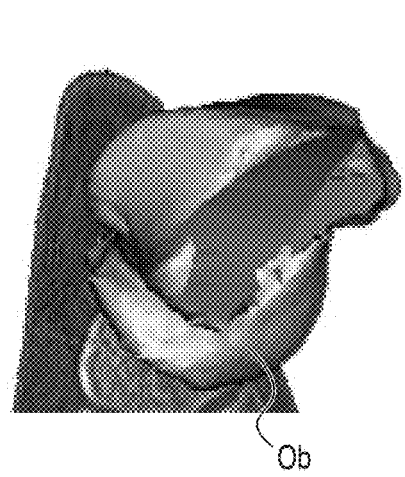
FIGS. 7A-7B show examples of the locations and orientations on the inferior, lateral posterior portions of the talus bone on which its talar component can be affixed.
Figure 7B:
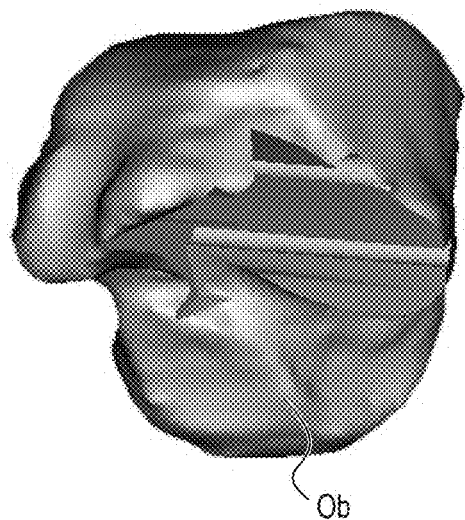

The exact nature of the placement and orientation of these adjoining talar 2 and calcaneal 4 components in the foot can vary widely depending upon the wide range of pathologies that can be encountered in patients needing subtalor joint replacement surgery. For example, shown in FIGS. 6A-6B are examples of the locations and orientations on the superior, medial, anterior portions of the calcaneus bone on which its calcaneal component can be affixed. Similarly, shown in FIG. 7A-7B are examples of the locations and orientations on the inferior, lateral posterior portions of the talus bone on which its talar component can be affixed.

To facilitate fixation of the calcaneal component to the calcaneus, protrusions 30 extend from its inner surface 28. Depending on the direction of this component's insertion, these protrusions can either be aligned along that direction of insertion or may be aligned slightly obliquely to that direction.

In this preferred embodiment, these talar 2 and calcaneal 4 components are lateral to medially or posteriorly to anterior implanted in the patient at a location where the talus' inferior surface and the calcaneus' superior surface have reciprocal and corresponding curvatures (e.g. convex on concave or concave on convex).

In general, a patient's natural subtalar joint is resected so as to form a void, joint space that can accept the present invention's implant. This yields a linear gradient of curvature throughout the joint space, with a larger radius of curvature on the space's lateral side. The implant's radius of curvature may also vary in a non-linear manner, e.g., such that it assumes its largest value on the lateral side of the component, its smallest value at a mid-thickness point and an in-between value on the medial side of the component. This pinching down of the radius towards the center of the joint would be intended to mimic the bicondylar shape of the subtalar joint. In this instance only the shape of the inner surfaces of the implants would be affected.

These implant components may be manufactured from any combination of synthetic or biologic materials. A preferred embodiment of the implant components would be single, solid pieces composed of polyethylene (e.g., high density, ultra-high molecular weight polyethylene because of its excellent wear resistance and a low coefficient of friction) or other suitable plastic material and metal layers (e.g., titanium or cobalt chrome alloys), possibly bonded with titanium or tantalum. The implant's inner or bone-facing surfaces will generally be metallic or metallic combined with natural/biologics, while its outer layer would be a plastic material.

A variation of this includes the situation in which the implant components are made of separate material layers (e.g., an inner layer that includes the component's inner surface and an outer layer that includes the component's outer surface) that are temporarily or detachably locked together in place. The advantage of this is that if the component's outer layer of polyethylene shows considerable wear after years of use, the patient would undergo another procedure where the outer polyethylene layer would be replaced without excessive trauma to the surrounding anatomy. To identify when such a replacement might be necessary, one or several of the components may have markers or indicators or electronic devices that can give feedback on the state of the implant components, including visualization, information about the amount of wear, or the presence of fractures (i.e., the wear life of the implants could conceivably be addressed by a routine replacement procedure).

To gain lateral access to the subtalar joint, an incision can be made along the lateral side of the ankle and hindfoot. The muscles and contents of the sinus tarsi region of the foot are elevated, reflected, and refracted, exposing the subtalar joint.

Next, a guidewire is inserted into the lateral side of the foot, into the sinus tarsi and then into the tarsal canal between the talus and calcaneus bones. The guidewire is further inserted until the medial skin is tented. A relief incision is then made on the medial side of the foot and the guidewire passed out the medial side of the foot.

The previously mentioned surgery aiding jig or device 40 is positioned on the medial aspect of the hindfoot. A sleeve is inserted over the aforementioned guidewire so as to protect the neurovascular structures on the medial side of the foot. A stylus is then passed through the sleeve and used to determine the arc and contour of the subtalar joint.

Once this is determined, this arc, along with possible other anatomic landmarks, such as the superior apex of the posterior facet of the subtalar joint, are used to further align the jig, which is then definitively fixed to either the lateral or medial side of the foot, and secured by one or more pins and/or screws inserted through the device into the bones of the foot and/or lower leg. Additionally, a laser light or alternative technical aid may be used to project the positions of the anatomic landmarks and thus facilitate the positioning of the instruments and surrounding apparatus.

In the situation where there is gross malalignment or missing or damaged bone, the joint space may have to be manipulated with shims or distracters used to realign or distract the joint space in accordance with normal relationships. Once proper alignment and height is achieved, taking into consideration unhealthy or non-viable bone, the tool set is placed according to these new anatomic landmarks, according to previously described steps.

A cutting head apparatus is secured to the device's base 42. Through or around this cutting head apparatus are passed the instruments that allow for precise joint preparation entailing removal of the articular surface and varying degrees of subchondral bone, with the removed bone usually approximately matching our pre-determined implant shape and as closely as possible the normal joint contour. The instruments used to prepare the joint may include, but are not limited to: routers, reamers, chisels, osteotomes, and serrated or abrasive saw blades.

This device's ball and socket joint 46 allows translation and/or rotational positioning changes of the cutting head apparatus. The device's guide 48 is used to guide the cutting instruments and may include, but is not limited to, one or some combination of the following: defined slots in the cutting jig; an articulating cutting guide, and a pivot mechanism.

Once the cutting head apparatus is fixed in the desired position, the cutting instrument is passed through the ball and socket joint 46. For example, a router may be swept back and forth to prepare the joint. This allows a reproducible method for minimizing bone loss while performing accurate bone cuts. The precision of this technique follows the contours described by the implant shape, allowing for the preservation of the strongest portions of the distal talus and proximal calcaneus.

Once the arc and contour of a patient's subtalar joint are assessed, the required size and dimensions of the needed portion-of-the-boundary-surface-of-a-frustum shaped implant can be determined and the surgery aiding jig properly positioned. For example, the height of this frustum's apex above its base can be used to locate the jig's mounting mechanism at a comparable height (i.e., at the apex of the cone implied by the implant's shape) above the new joint space that is to be created to accommodate the implant. The guide 48 is centered at this apex point which then serves as a tool pivot point for creating the new joint space.

Figure 8A:
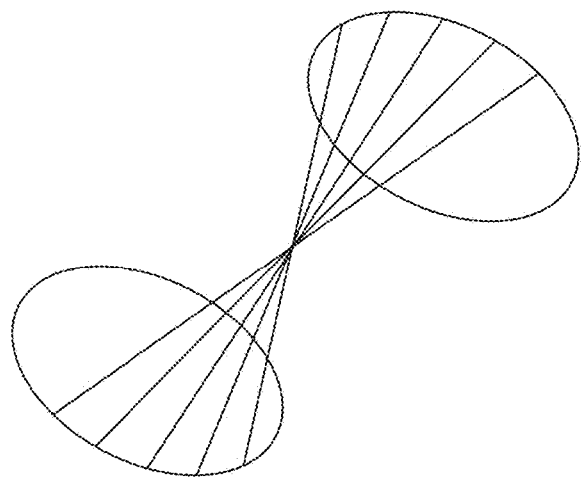
FIG. 8A illustrates the motions of the shafts of the cutting tools used to create the joint space for a preferred embodiment of the present invention.
Figure 8B:
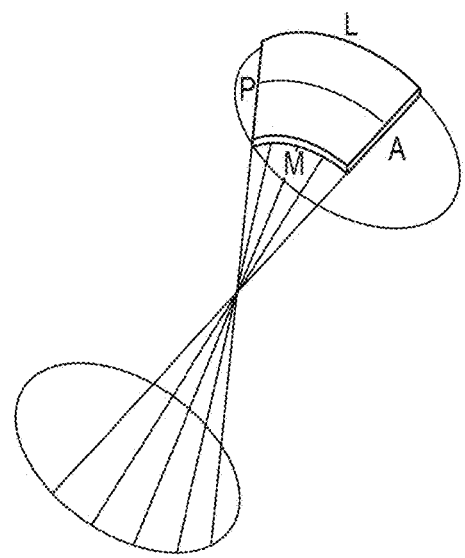
FIG. 8B shows ordered arrows showing the path necessary for a cutting tool to create a portion-of-the-boundary-surface-of-a-frustum shaped joint space.

The shafts of any cutting tools are moved along reciprocating conical motions in front and behind this pivot point. See FIGS. 8A-8B, where FIG. 8A shows the paths that may be taken by the tool shaft and the opposing arcs resulting from these paths, and FIG. 8B illustrates ordered arrows showing the path necessary for the tool to cut out the desired shape.

In addition to the medial and lateral jig approaches, a combination jig may also be used. Such a combination approach involves a ball and socket pivoting and guiding mechanism with a solid shaft passing through it. This pivoting mechanism is fixed medial to the joint and the shaft is passed through the tarsal canal. The purpose of these elements is only to guide the motion of the cutting tool, which is positioned lateral to the joint. The cutting tool used with this approach has a hollow shaft with rough, cutting protrusions towards the end of the shaft and with this shaft placed concentrically around the guiding shaft from the medial side. Again, similar to the medial approach this jig requires prior distraction of the joint space. The main advantage of this approach is that it allows for support of the tool shaft from both sides, leaving it less vulnerable to bending moments/deflections.

The foregoing is considered as illustrative only of the principles of the invention. Further, since numerous modifications and changes will readily occur to those skilled in the art, and because of the wide extent of the teachings disclosed herein, the foregoing disclosure should not be considered to limit the invention to the exact construction and operation shown and described herein. Accordingly, all suitable modifications and equivalents of the present disclosure may be resorted to and still considered to fall within the scope of the invention as set forth in claims to the present invention.

We claim:

1. A subtalar joint prosthesis adapted to replace the natural subtalar joint that exists between a patient's talus and calcaneus bones after appropriate surgical preparation of the appropriate joint-related inferior portions of said talus and the superior portion of said calaneus so as to accommodate said prosthesis, said prosthesis comprising:

a talar component having an inner and an outer surface and medial and lateral sides, and wherein said talar component inner surface is configured to generally follow the anatomic contour of said inferior portion of said talus surface to which said talar component is to be attached, and wherein said talar surfaces and sides are configured such that said talar component is portion-of-the-boundary-surface-of-a-frustum shaped and with said frustrum that provides this shape being formed from a cone whose apex lies on a side chosen from the group consisting of the medial and lateral sides of said joint so as to provide said talar component with a configuration that allows for said talar component to be inserted in a direction chosen from the group consisting of lateral to medial and medial to lateral, a calcaneal component having an inner and an outer surface and medial and lateral sides, and wherein said calcaneal component inner surface is configured to generally follow the anatomic contour of said superior portion of said calcaneus surface to which said calcaneal component is to be attached, and wherein said calcaneal surfaces and sides are configured such that said calcaneal component is portion-of-the-boundary-surface-of-a-frustum shaped and with said frustrum that provides this shape being formed from a cone whose apex lies on a side chosen from the group consisting of the medial and lateral sides of said joint so as to provide said calcaneal component with a configuration that allows for said calcaneal component to be inserted in a direction chosen from the group consisting of lateral to medial and medial to lateral, and wherein said talar and calcaneal outer surfaces having complimentary geometries so as to allow said talar and calcaneal outer surfaces to move with respect to one another in such a manner as to simulate the motion in said patient's natural subtalar joint.

2. The subtalar joint prosthesis as recited in claim 1, wherein:

said talar component having a herein defined average thickness, $t_T$, that quantifies the average distance between said talar component inner and outer surfaces, and wherein said talar component surfaces are configured so that said talar component average thickness, $t_T$, assumes a minimum value so as to yield a minimal amount of bone resection from said inferior portion of said talus while providing sufficient strength and rigidity in said talar component.

3. The subtalar joint prosthesis as recited in claim 1, wherein:

said calcaneal component having a herein defined average thickness, $t_C$, that quantifies the average distance between said calcaneal component inner and outer surfaces, and wherein said calcaneal component surfaces are configured so that said calcaneal component average thickness, $t_C$, assumes a minimum value so as to yield a minimal amount of bone resection from said superior portion of said calcaneus while providing sufficient strength and rigidity in said calcaneal component.

4. The subtalar joint prosthesis as recited in claim 2, wherein:

said calcaneal component having a herein defined average thickness, $t_C$, that quantifies the average distance between said calcaneal component inner and outer surfaces, and wherein said calcaneal component surfaces are configured so that said calcaneal component average thickness, $t_C$, assumes a minimum value so as to yield a minimal amount of bone resection from said joint-related portion of said calcaneus while providing sufficient strength and rigidity in said calcaneal component.

5. The subtalar joint prosthesis as recited in claim 1, wherein:
   said talar component inner surface having protrusions adapted to affix said component to said prepared, joint-related portions of said talus.

6. The subtalar joint prosthesis as recited in claim 4, wherein:
   said talar component inner surface having protrusions adapted to affix said component to said prepared, joint-related portions of said talus.

7. The subtalar joint prosthesis as recited in claim 1, wherein:
   said calcaneal component inner surface having protrusions adapted to affix said component to said prepared, joint-related portions of said calcaneus.

8. The subtalar joint prosthesis as recited in claim 4, wherein:
   said calcaneal component inner surface having protrusions adapted to affix said component to said prepared, joint-related portions of said calcaneus.

9. The subtalar joint prosthesis as recited in claim 5, wherein:
   said calcaneal component inner surface having protrusions adapted to affix said component to said prepared, joint-related portions of said calcaneus.

10. The subtalar joint prosthesis as recited in claim 6, wherein:
    said calcaneal component inner surface having protrusions adapted to affix said component to said prepared, joint-related portions of said calcaneus.

11. The subtalar joint prosthesis as recited in claim 1, wherein:
    said component outer surfaces having complimentary geometry so as to allow said components to have a defined level of constraint of movement with respect to one another and while simulating the motion in said patient's subtalar joint.

12. The subtalar joint prosthesis as recited in claim 4, wherein:
    said component outer surfaces having complimentary geometry so as to allow said components to have a defined level of constraint of movement with respect to one another and while simulating the motion in said patient's subtalar joint.

13. The subtalar joint prosthesis as recited in claim 10, wherein:
    said component outer surfaces having complimentary geometry so as to allow said components to have a defined level of constraint of movement with respect to one another and while simulating the motion in said patient's subtalar joint.

14. The subtalar joint prosthesis as recited in claim 1, wherein:
    at least one of said components having material layers that are detachably locked together, said layers including an inner layer that includes said component inner surface and is made from a metallic material and an outer layer that includes said component outer surface and is made from a plastic material.

15. The subtalar joint prosthesis as recited in claim 4, wherein:
    at least one of said components having material layers that are detachably locked together, said layers including an inner layer that includes said component inner surface and is made from a metallic material and an outer layer that includes said component outer surface and is made from a plastic material.

16. The subtalar joint prosthesis as recited in claim 10, wherein:
    at least one of said components having material layers that are detachably locked together, said layers including an inner layer that includes said component inner surface and is made from a metallic material and an outer layer that includes said component outer surface and is made from a plastic material.

17. The subtalar joint prosthesis as recited in claim 13, wherein:
    at least one of said components having material layers that are detachably locked together, said layers including an inner layer that includes said component inner surface and is made from a metallic material and an outer layer that includes said component outer surface and is made from a plastic material.

* * * * *